United States Patent [19]
Brunelli et al.

[11] Patent Number: 5,412,738
[45] Date of Patent: May 2, 1995

[54] RECOGNITION SYSTEM, PARTICULARLY FOR RECOGNISING PEOPLE

[75] Inventors: Roberto Brunelli, Trento; Daniele Falavigna, Buttapietra, both of Italy; Tomaso Poggio, Wellesley, Mass.; Luigi Stringa, Villazzano, Italy

[73] Assignee: Istituto Trentino Di Cultura, Trento, Italy

[21] Appl. No.: 103,700

[22] Filed: Aug. 10, 1993

[30] Foreign Application Priority Data

Aug. 11, 1992 [IT] Italy .................. TO92A0695

[51] Int. Cl.⁶ .................................. G06K 9/00
[52] U.S. Cl. ........................ 382/115; 381/41; 382/209
[58] Field of Search .......................... 382/2–5, 382/30, 34; 340/825.34; 348/152, 156, 143; 381/41, 42

[56] References Cited

U.S. PATENT DOCUMENTS

| | | | |
|---|---|---|---|
| 4,449,189 | 5/1984 | Feix et al. ............... | 382/2 |
| 4,993,068 | 2/1991 | Piosenka et al. ........ | 382/2 |
| 5,187,574 | 2/1993 | Krosemura et al. ..... | 382/2 |
| 5,202,929 | 4/1993 | Lemelson ............... | 382/2 |
| 5,229,764 | 7/1993 | Machett et al. ......... | 340/825.34 |

FOREIGN PATENT DOCUMENTS

| | | |
|---|---|---|
| 0386846 | 9/1990 | European Pat. Off. . |
| 4031089 | 4/1992 | Germany . |
| 2202942 | 10/1988 | United Kingdom . |
| 2251058 | 6/1992 | United Kingdom . |

OTHER PUBLICATIONS

"Comparison of Parametric Representations for Monosyllabic Word Recognition in Continuously Spoken Sentences" by S. B. Davis and P. Mermelstein; IEEE TRansactions on Acoustic, Speech and Signal Processing, vol. 28, No. 4, Aug. 1980, pp. 357–364.

"Vector Quantization in Speech Coding" by J. Makhoul, S. Roucos, H. Gish, Proc. IEEE, vol. 73, No. 11, Nov. 1985, pp. 1551–1588.

Primary Examiner—Joseph Mancuso
Attorney, Agent, or Firm—Banner, Birch, McKie & Beckett

[57] ABSTRACT

An integrated, multisensory recognition (identification and verification) system is described. Acoustic features and visual features are integrated in order to identify people or to verify their identities. The integration of the speaker-identification and visual-features-identification functions improves both performance and reliability in the applications envisaged. Various architectures are described for the implementation both of the integration function and of the speaker-recognition and visual-features-recognition functions.

24 Claims, 2 Drawing Sheets

RECOGNITION SYSTEM, PARTICULARLY FOR RECOGNISING PEOPLE

BACKGROUND OF THE INVENTION

The present invention relates in general to recognition systems, particularly for recognising people.

The term "recognition" as used in the present description and, where appropriate, in the following claims, should be understood by its generally accepted meaning which includes, amongst other things, both the function currently known as "identification" the detection of the features of a person, the comparison of the data relating thereto with data, relating to identifying features of a plurality of people, stored in a data bank, and the subsequent identification of the person as one of the people whose features are stored in the data bank) and the function currently known as "verification" (ascertaining whether the features of the person being checked correspond to identification data previously stored and used as a template for comparison).

Recognition systems of the type specified above can be used, for example, for controlling access, for example, for "electronic concierge functions", in order to recognise employees working in small organisations (about 100 people); in this case small percentages of errors in the identification function are permitted.

Alternatively, systems of the type specified above may be used as systems for directly verifying and precisely ascertaining the identity of a certain person, whose identifying features are stored in the form of a template. In this case, however, it is not simply a question of checking to which of a plurality of previously stored templates the person in front of the system most probably corresponds, but, on the contrary, involves ascertaining in almost absolute terms that the person whose features are examined actually corresponds to a given person, for example, the only person or one of the few people authorised to have access to a certain area or to a certain service. A typical example of the application of a system of this type is that of controlling the opening of the door, for example, of a dwelling to which, naturally, it is desired to allow free access solely to residents. In these cases errors in recognising people are wholly unacceptable.

Naturally, the examples given above are only two of the possible applications of systems of the type specified above. These systems may be used, for example, for carrying out alternative (or additional) functions in relation to the supply of a password for access to a certain service, for example, by means of a terminal of a data-processing system, or even for systems for carrying out transactions automatically, such as electronic banking machines (BANCOMAT etc.). Clearly, in all the applications described above, the minimising of the possible margins of error is an imperative requirement.

SUMMARY OF THE INVENTION

In general, the following description will refer, almost without differentiation, to the identification and verification functions both of which are included in the more general category of recognition functions. The characteristics intrinsic in the performance of the two different functions described above correspond to two different modes of operation (in practice, to the programming for two different modes of operation) of a system which retains almost the same structural and functional characteristics.

The object of the present invention is essentially to provide a recognition system which can perform the identification and verification functions in an optimal manner, reducing the probabilities of error to a minimum, particularly in the performance of the verification functions, without thereby involving extremely complex circuitry, thus providing recognition units of reasonably low cost, which can be used on a large scale.

According to the present invention, this object is achieved by virtue of a system having the specific characteristics recited in the following claims.

In summary, the solution according to the invention provides an automatic people-recognition system which uses both acoustic characteristics derived from the analysis of a speech signal, and visual characteristics connected with distinguishing parameters of the face of the person uttering the speech signal.

In principle, the two subsystems of which the system is composed (the acoustic and visual systems) may also be used individually.

The system may be used both for identification functions and for verification functions. The description given below will refer principally to the identification function; however, as already stated, the same considerations also apply to verification applications.

An important characteristic of the solution according to the invention is the way in which the two sets of data, that is, the acoustic and visual data, are combined at various levels; experiments carried out by the Applicant have shown that the two subsystems cooperate in a synergistic manner to achieve a significant improvement in overall performance.

The acoustic subsystem, which can be defined as a speaker-recognition system (or SRS), uses acoustic parameters computed from the spectra of short time windows of the speech signal. This method is described in general terms in the article "Comparison of Parametric Representations for Monosyllabic Word Recognition in Continuously Spoken Sentences" by S. B. Davis and P. Melmerstein; IEEE Transactions on Acoustic, Speech and Signal Processing, Vol 28, No. 4, August 1980, pp. 357–366.

The system compares the spectral vectors derived from the input signal with prototypical vectors which are stored in the system and which represent each of the speakers to be recognised. The prototypical vectors are determined by applying the "vector quantization" technique to a sufficiently large set of data characteristic of the speakers details (in this connection, see the article "Vector Quantization in Speech Coding" by J. Makhoul, S. Roucos, H. Gish, Proc. IEEE, Vol. 73, No. 11, November 1985, pp. 1551–1588.

As far as the visual, face-recognition system (or FRS) is concerned, various solutions may be used.

For example, it is possible to start with geometrical criteria, by computing a vector which describes discriminating facial features such as the position and width of the nose, the shape of the cheek bones, and so on, extracted in real-time from a frontal image of the face.

Alternatively, it is possible to use an iconic system in which the recognition is effected by comparison with models ("templates") of the entire face or of some distinguishing regions of the face.

As regards the combination of the acoustic and visual subsystems, the results obtained may be combined at various levels.

A first level is that of the similarity estimates (or distance estimates: in effect, these are two measurements which are, in broad terms, inversely proportional and which characterize essentially the same concept) produced by the two subsystems independently; these estimates are used in a classification system (for example, with weighting and optimised addition) so as to produce a single final result on which to base the decision.

Alternatively, it is possible to proceed at the level of the measurements made on the vocal and visual signals; the vector of the acoustic input parameters, the geometric vector relating to the visual parameters and, jointly with or as an alternative to the latter, the vector resulting from the direct (iconic) comparison of regions of the face, are considered as a single vector (for example, by taking the cartesian product of the acoustic and visual distances). This vector is then classified by means of a specific classifier which may be constituted by a net which can approximate the characteristic function of the speaker; for example, a Bayes classifier, a multilayer Perceptton classifier, or a Radial Basis Function classifier.

BRIEF DESCRIPTION OF THE DRAWINGS

The invention will now be described, purely by way of non-limiting example, with reference to the appended drawings, in which.

DETAILED DESCRIPTION

Figure 1:
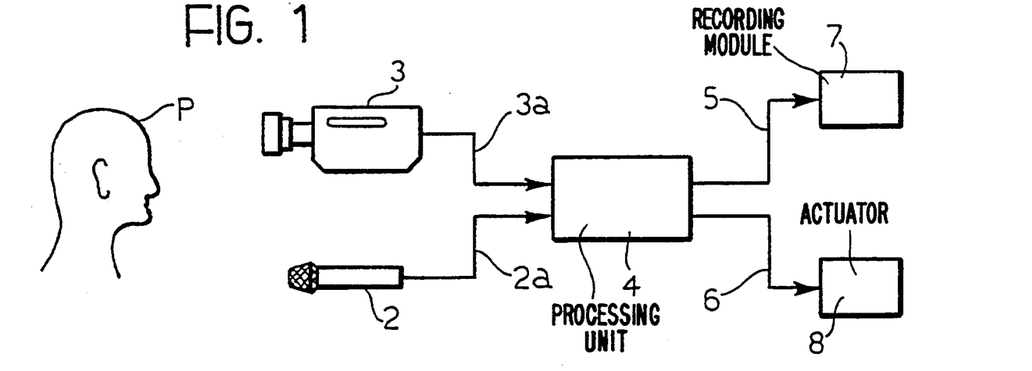
FIG. 1 shows a typical configuration of a system according to the invention.

In summary, the system according to the invention, generally indicated 1, comprises an acoustic detector such as a microphone 2, and a visual or optical detector, such as a television camera 3, disposed in a manner such that, in use, they face the person P to be recognized.

The microphone 2 and the television camera 3 are widely known devices. The microphone 2 may be a conventional microphone, for example, of the type used in intercom systems (although the use of a better-quality microphone may be beneficial for the purposes of greater resolution in detecting the vocal features), and the television camera 3 may be, for example, a CCD television camera (usually black and white or, possibly, even a colour camera).

Naturally, for the purposes of the following description, the microphone 2 and the television camera 3 are considered to include all the interface and auxiliary elements (supply circuits, amplifiers, saturation-protection circuits, signal-conditioning circuits, etc.—which are not shown explicitly in the appended drawings, since they are known and in any case are irrelevant for the purposes of an understanding of the invention) which enable them to send signals in a format suitable for subsequent processing to the processing core 4 which constitutes the heart of the system. For example, the microphone 2 and the television camera 3 may be equipped with analogue to digital converters so that the output signals supplied thereby are already in the form of digital signals.

The processing unit 4 outputs signals corresponding to the recognition (identification, verification, etc.) of the person P which is effected on the basis of the signals generated by the microphone 2 and by the television camera 3.

For clarity of illustration, it has been assumed, in general, that the processing unit 4 has a plurality of output lines (which may possibly be integrated in a single output line controlled in a serial manner). Two output lines 5, 6 are shown in FIG. 1 with the intention of indicating the fact that, as a result of the recognition, the unit 4 can, jointly or alternatively:

generate a signal (line 5) which transmits information relating to the recognition effected to a recording module 7 which stores this information (for example, in order to check the time at which a certain person arrives at or leaves a certain area for recording purposes);

generate an actuation signal (line 6) which is intended to be sent to one or more actuators 8 for activating certain devices (for example the lock which controls the opening of a door, any member which enables the activation or use of a certain device or service, such as, for example, a terminal of a data-processing system etc.) in accordance with the recognition effected.

Figure 2:
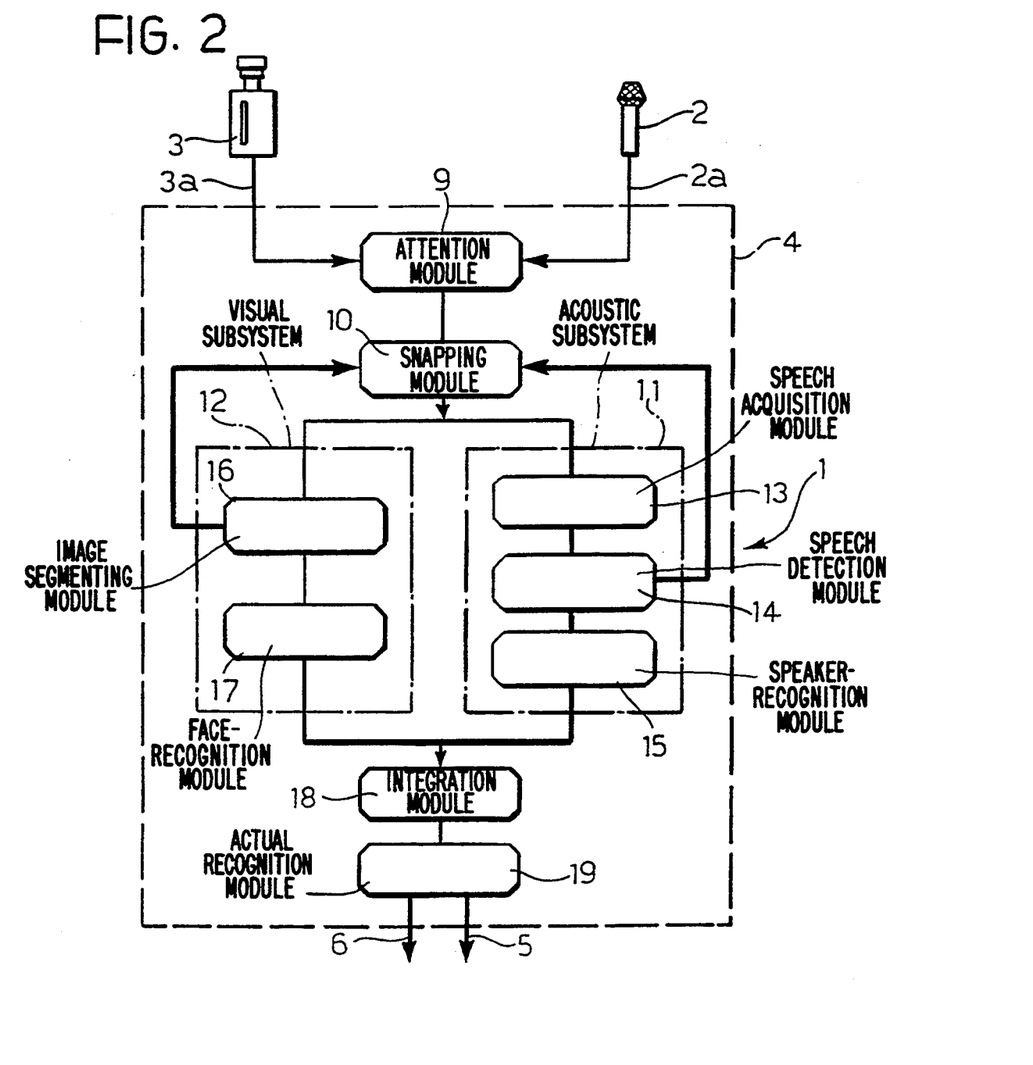
FIG. 2 is a functional block diagram showing the processing core of the system.

FIG. 2 shows in greater detail the structure of the processing unit 4 which may, for example, be implemented in the form of a microprocessor system or by means of a miniprocessor, or even by a dedicated function of a more complex processing system; however, the use of one of these selections from a range which, moreover, should not be considered exhaustive (in fact, it is possible to consider the use of different processing systems, for example, having parallel or neural architecture, etc.), is not limiting per se for the purposes of putting the invention into practice.

Moreover, it should be stated that the structure of the processing unit 4 will be described with reference to functional blocks or modules. As is well known to an expert in the art, these may either be in the form of actual separate blocks or—according to a solution which is usually considered preferable—may be functions implemented within a processing system.

The detection signals produced by the microphone 2 and by the television camera 3 are sent on respective output lines 2a and 3a to a so-called attention module 9, the function of which is essentially to determine when a person P is in front of the system 1 for recognition.

The attention module 9 is sensitive primarily to the signal supplied by the television camera 3. This camera is configured (in known manner) so that it can detect changes in the scene framed, with the use of background-subtraction and thresholding techniques implemented, for example, in the module 9.

An identical function could also be carried out on the vocal signal coming from the microphone 2. It would also be possible to consider integrating the two activity signals produced in the attention module 9. In any case, the tests carried out by the Applicant show that the piloting of the attention function by the visual signal produced by the television camera 3 and the subsequent awakening of the acoustic-detection function according to the criteria described further below, constitutes a wholly satisfactory functional selection.

With specific reference to this latter solution, when the module 9 detects the fact that the scene framed by the television camera 3 has changed, probably due to the arrival of a person P in front of the system for recognition, the module 9 activates a further module 10 which may be defined as a snapping module. The function of the module 10 is essentially to wait until the scene in front of the television camera 3 has stabilised (for example, because the person P who wishes to be identified has stopped in front of the television camera 3), and also to check that certain elementary conditions are satisfied (typically, as regards the total amount of change detected, so as to be able to prevent recognition from starting unnecessarily, simply as a result of an object or a person passing or stopping momentarily in front of the system).

When the module 10 has verified the existence of the conditions of stability of the image framed which are prescribed in order for initiation of the recognition step to be considered likely, it activates the two subsystems 11 and 12 which carry out the actual recognition.

Essentially, these are an acoustic subsystem 11 for operating on the vocal signal supplied by the microphone 2 and a visual sub-system 12 for operating on the video signal supplied by the television camera 3.

In this connection, the video signal acquired by the module 10 is supplied directly to the image-recognition subsystem 12 and, at the same moment, the system asks the person P, by means of an acoustic indicator or a loud speaker (which is not shown but may be integrated in the microphone 2) to utter certain words, for example, isolated digits in any order.

At this point, the subsystem 11 and, in particular, a speech acquisition module 13 for acquiring the vocal signal, is activated. The vocal signal thus acquired is sent to a speech detecting module 14 which identifies the end points of the message uttered, particularly the start and the finish of the sound signal, as well as a certain number of speech segments with the corresponding durations, to be processed in a manner described further below. If the overall duration of the speech segments detected by the module 14 is not long enough, the system is reactivated from the beginning, for example, by asking the person P to speak again.

If, after the system has been activated, no vocal signal is detected, the system is usually returned to the starting condition, possibly with a pause.

If, however, the vocal signal is confirmed by the module 14 as usable for the recognition function, the signal is passed to a further speaker-recognition module 15 the structure of which will be described further below.

In parallel, the visual signal produced by the television camera 3 and passed through the modules 9 and 10 is transferred to the subsystem 12 which comprises essentially two modules, that is to say, an image segmenting module 16 for segmenting the image of the face of the person P and a recognition module 17. The details of the construction of these two modules and, in particular, of the face-recognition module 17 will be described below.

The recognition signals produced in the two subsystems 11 and 12 are transferred to an integration module 18 which combines the recognition signals from the two subsystems in a synergistic manner so as to optimise the effectiveness of the recognition. The results of the combination effected in the module 18 are transferred to an actual recognition module 19 from which the output lines 5 and 6 of the system extend.

The operating criteria of the various functional modules described above will be described below in greater detail. In particular, the characteristics and construction of the activation subsystem comprising the modules 9 and 10, of the speaker-recognition subsystem 11, and of the image-recognition subsystem 12 will now be described. Finally, the operation and construction of the integration and recognition system comprising the modules 18 and 19 will be described in detail.

The activation subsystem

As has been seen, this subsystem is intended to be activated automatically when the presence of a person P is detected in the area monitored.

In practice, the television camera 3, together with the attention module 9, is constantly in an alert condition so as to be able to detect any changes in the scene framed. Gradual changes in ambient illumination are taken into account automatically by the operation of the diaphragm of the television camera 3 so as to obtain correctly exposed images, for example, by maximising the entropy of the image acquired or by using any other technique suitable for the purpose. Whenever the television camera detects a certain amount of change (either in intensity or as regards surface, above predetermined thresholds) in comparison with the background reference image (which is updated with every adjustment of the diaphragm) the system is put in a state of alert and waits for the image to stabilise (by means of the snapping module 10) by checking the changes between successive frames.

Whenever the image stabilises, simple checks are made on the area of the changes in the image to ensure that the approximate dimensions of the object framed are consistent with those of a face at a standard distance.

At this moment, as has been seen, the module 10 acquires an image from the television camera 3 (as though a photograph were taken) and activates the recognition subsystems.

The recognition subsystems

These subsystems, which are generally indicated 11 and 12 in FIG. 2, may be formed on hardware boards of various types. In general, both the subsystems 11 and 12 operate in two steps. In the first place, one or more descriptive vectors are extracted from the vocal or visual signal.

A procedure based on distance measurements (matching) is then applied to these vectors to evaluate their similarity to the models stored in the data bank of the system; this comparison generates two lists of partial scores or results, one for each subsystem.

The speaker-recognition subsystem

As stated in general at the beginning of the present description, speaker recognition may take the form either of a verification of the speaker's identity, or of an identification of the speaker.

A speaker-identification system has to determine which person of a known group of people uttered the input speech signal.

A speaker-verification system checks (by confirming or not confirming) the identity of a person, for example, before giving access to a reserved location or service.

Speaker-recognition systems may be either text-dependent (in this case the user must utter a certain vocal sequence, for example, a certain word, a certain phrase, or certain digits) or may be independent of the text.

In general, within the module 15 (see the block diagram of FIG. 3 in particular) the input signal coming from the microphone 2 (through the modules 9 and 10) is sent to the input of a first block 20 for extracting acoustic parameters (feature extraction).

Figure 3:
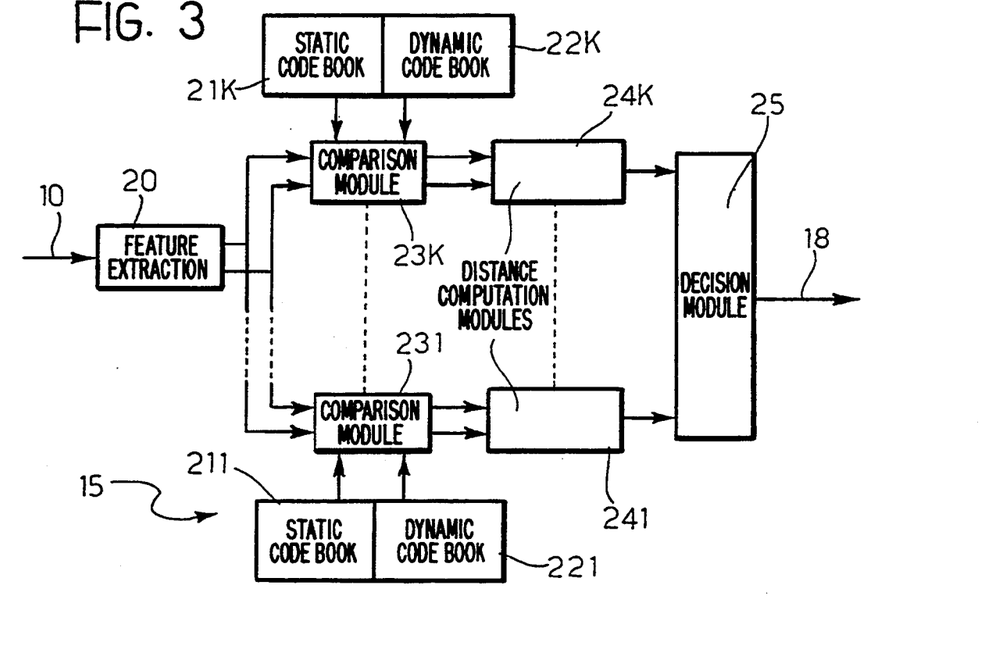
FIG. 3 shows the structure of one of the subsystems included in the system according to the invention, also in the form of a block diagram.

For this purpose, the signal is first pre-emphasized with the use of a digital filter, for example, with a transfer function of the type $H(z)=1-0.95 \times Z^{-1}$. The pre-emphasized signal is analyzed every 10 milliseconds with the use of a 20 millisecond Hamming window, the following parameters being computed for each window:

- eight Mel cepstral coefficients (in this connection, see the article by Davis and Melmerstein already mentioned) computed with the use of a bank of 24 triangular pass-band filters spaced in frequency according to a logarithmic scale; these parameters may be called static parameters, since they relate to a single voice-signal analysis window;
- the corresponding first-order time derivatives; these are computed by means of a first-order polynomial fit on nine windows (frames) of static parameters centred on the given analysis window; the latter parameters are defined as dynamic parameters.

The parameters thus obtained are intended to be subjected, in the manner which will be described further below, to a recognition operation which, in general terms, is carried out by comparing the vectors of parameters computed from the sound signal sample detected at any particular time with the data collected in a data bank within the system.

This data bank may be viewed essentially as a collection of templates (that is, sets of vectors of parameters corresponding to the speakers to be recognised) arranged in two codebooks: one for the static parameters and the other for the dynamic parameters, as described above.

In general, the subsystem 11 and, in particular, the module 15, contains a number of pairs of these codebooks equal to the number of speakers to be identified or checked.

For example, FIG. 3 shows a first pair of codebooks 211, 221 for collecting the static and dynamic template parameters of a first speaker, respectively, whilst the corresponding two codebooks relating to the K-th speaker are indicated 21K, 22K.

Naturally, in identification systems (in the terms cited in the introduction to the description) K may have a fairly high value (100 or more). In verification systems, however, K usually has a much lower value, at most a few units if not even a unitary value in the case of systems for verifying the identity of one person (communicated to the system by means of a different channel) who requires access to a certain area or service.

In exactly the same way, the reference numerals 231, 23K identify the units which carry out a first stage of the comparison between the vectors of static and dynamic parameters coming from the block 20 and the vectors of reference parameters stored in the code books 211 ... 21K and 221 ... 22K, respectively with reference to speakers 1 to K.

Comparison

In cascade with the modules 231 ... 23K are corresponding distance computation modules 241 .... 24K which carry out distance computations. The results of the operations carried out in the distance computation modules 241 ... 24k are analysed in a decision module 25 which outputs to the integration module 18 the data relating to the distance computed by the subsystem 11 operating on the speech signal.

In order to generate the reference codebooks 211 ... 21K and 221 ... 22K, it is possible to apply, for example, Linde-Buzo-Gray's algorithm (in this connection see J. Makhoul, S. Roucos, H. Gish, "Vector Quantization in Speech Coding", Proc. IEEE, Vol. 73, No. 11, November 1985, pp 1551–1588) to the vectors (static and dynamic) derived from a series of recording sessions carried out for each speaker to be recognised.

In general, in fact, the system according to the invention (whether it operates as an identification system or as a verification system) is initially trained by detecting samples of the vocal signal of the person to be recognised, in order to form the internal data bank constituted by the codebooks 211 ... 21K and 221 ... 22K.

The distance measurement used both to form the codebooks 211 ... 21K and 221 ... 22K and to carry out the recognition is a weighted Euclidjan distance in which the weightings are the inverse of the variances of the components of the training vectors averaged over all the training recordings and over all the speakers.

Consequently, if $\theta_i$ and $\Psi_i$ are the two parametric vectors, their distance is defined as $$d^2(\theta_i, \psi_i) = \sum_{k=1}^{P} \frac{1}{\sigma_k^2} (\theta_{ik} - \psi_{ik})^2 \quad (I)$$

where $\sigma_k^2$ is the average variance of the K-th component of the vector of the parameters.

In an embodiment which has been found particularly advantageous, p is selected so as to be 8.

In practice, in order to recognise the speech message, the static and dynamic vectors processed by the module 20 at the time in question (assuming that these are represented by $\theta_{ik}$) are compared with the static and dynamic vectors (which may be assumed to be represented by $\Psi_{ik}$) in all the codebooks 211 ... 21K and 221 .... 22K.

Each module 231 ... 23K therefore outputs the respective distances (evaluated according to formula I above) to the modules 241 .... 24K which compute, by arithmetical methods, the overall distortion (static distortion + dynamic distortion) detected between the vocal signal input and the template stored, for each different speaker to be recognised, in a respective pair of codebooks 21I, 22I.

Consequently, if $\Theta = \theta_1) \ldots, \theta_T$ is the static (or dynamic) input sequence and $\Psi_j = \Psi_{j1}, \ldots, \Psi_{jm}$ are vectors of the j-th static or dynamic codebook (where M is the spectral resolution), then the overall static (or dynamic) distortion is defined as:

$$D(\Theta, \psi_j) = \frac{1}{T} \sum_{t=1}^{t} \min_{i=1}^{M} d(\theta_t, \psi_{ji}) \quad (II)$$

In particular, within the modules 241 ... 24K, the static and dynamic distances are normalised with respect to their mean values computed over the set learned, and are added together.

Finally, the decision modules 25 and the integration modules 18, 19 examine the various distances computed and normalised by the modules 241 ... 24K, and then select the speaker recognised on the basis of the criteria described further below. For example, the criterion may advantageously be constituted by a minimum distance criterion. In practice, the module 25 recognises whether the speaker who uttered the sound message detected by the microphone 2 corresponds to the speaker whose static and dynamic parameters are stored in the codebooks 21$i$, 22$i$ for which the minimum distance value was computed by the respective module 24$i$.

Naturally, it is also possible to consider the use of other selection criteria.

The performance of the system depends both on the acoustic resolution (that is to say, on the number of elements contained in each book 21$i$, 22$i$) and on the duration of the vocal signal used for recognition.

The average identification error evaluated over a set of tests composed of 100 samples per speaker (the number of speakers being 42) was 48.6% for a spectral resolution of 4 and 5.3% for a spectral resolution of 64.

The visual recognition system

The recognition of people on the basis of their visual features is an operation normally carried out by each of us every day. The ease with which humans and also animals, recognise people familiar to them from their faces tends, perhaps, to make us undervalue the complexity of the problem. Some fairly extensive psychophysical experiments have shown that, even for humans, the recognition procedure requires quite complex processing and is in no way an innate ability: this ability increases during the first years of life as a result of the gradual integration of various strategies into the process.

As already stated, there are two basic strategies for the automatic recognition of faces; it can be stated that both these strategies simulate, to a certain extent, the processes normally used by humans.

The first strategy, which may be defined as the iconic strategy, is based on a comparison of suitably pre-processed regions of images; in this case, recognition is effected by comparing (for example, by means of a correlation coefficient which estimates the similarity of two images, or a suitable distance criterion, which estimates the difference between two images) an unknown image with stored templates of particularly distinctive facial characteristics of known people.

Another strategy, which may be defined as a geometric strategy, provides for the computation of a set of geometrical characteristics which describe the dimensions and shapes of the various characteristics of faces; in this case, recognition is carried out by comparing the descriptive vector derived from the image of the unknown person with a set of reference vectors (known people) stored in a data bank.

Various methods may be classified within this basic taxonomy. Both iconic strategies and geometrical strategies may be used within the system according to the invention. An embodiment of the subsystem 12 based on one geometrical strategy, and three strategies (and hence possible embodiments) based on iconic recognition will be described below. The latter strategies give rise to improved performance although they require greater computing and memory capacities.

Figure 4:
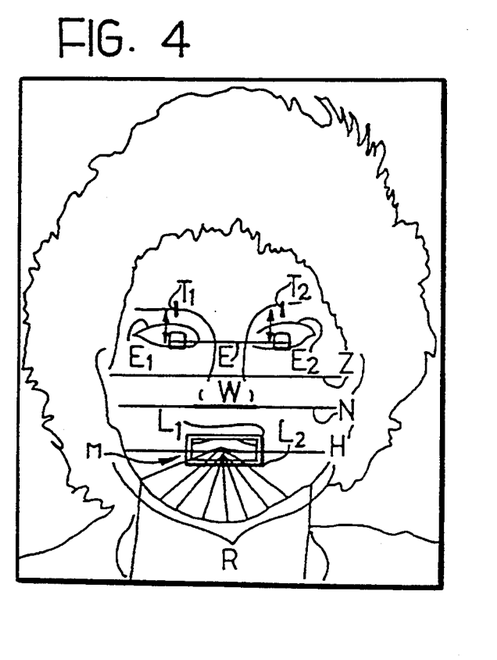
FIGS. 4 and 5 show schematically the criteria which can be used for carrying out the recognition function on the basis of visual features.

A first solution based on geometrical characteristics provides, in the first place, for the automatic computation of a set of geometrical characteristics which describe a front view of the face, by means of the following steps (see FIG. 4 in particular):

locating the eyes, so that the image can be standardised both as regards its dimensions and as regards its orientation (in the plane of the image);

using an average face template to focus the research of the system on the various parts of the face progressively in a sequential manner so as to be able to compute significant points of the facial characteristics;

constructing a descriptive vector from the relative positions of the significant points of the characteristics.

These steps may be carried out (according to known criteria which do not need to be described in detail herein) from the video signal received from the television camera 3, through the modules 9 and 10.

In particular, with reference to FIG. 4, it is possible automatically to compute a certain number of geometrical characteristics (even quite a large number, for example, 35 different characteristics) such as, for example:

the thicknesses $T_1$ and $T_2$ of the eyebrows and the distances $E_1$ and $E_2$ of the eyebrows from the interocular axis E in correspondence with the centres of the two eyes;

a general description of the arch of the left eyebrow (for example, 8 measurements);

the vertical position N of the nose and its width W;

the vertical position of the mouth M, its width, the thickness L1 of the upper lip and the thickness L2 of the lower lip L2, as well as the overall depth H of the mouth;

eleven radii R which describe the shape of the lower jaw;

the width Z of the face at cheekbone level; and the width of the face at nose level (identified by the line indicated N).

The classification may be based on a Bayes classifier.

As regards the processing of the data identified above (which are processed in the module 16), the module 17 preferably has architecture substantially similar to that of the module 15 described in detail with reference to FIG. 3 in relation to the identification of the speech signal.

In practice, in this case the signal (visual) is also compared with sample signals previously stored in the subsystem 12 during an initial learning stage, in order to derive—according to the methods described further below—respective factors relating to the distance between the signals detected at any particular time and the signals considered as samples, to enable an output selection module to identify the person framed as one of the people whose data have previously been stored and/or to verify that the person framed at the time in question actually corresponds to a certain person.

With reference to the method described above, which is based on a Bayes classifier, it is possible, by way of simplification, to infer that the measurements relating to the different characteristics have the same Gaussian distribution for all people, regardless of their average value.

The covariance matrix can thus be estimated and the classification can be based on the following distance, linked to the probability of the given measurement:

$$i: \Delta_i = \min_j \Delta_j \qquad \text{(III)}$$
$$\Delta_j^2 = (x - m_j)^T \Sigma^{-1} (x - m_j)$$

Thus, as in the case of the speaker-recognition system, the unknown vector is identified with the nearest one (the minimum distance in the data bank stored in the system).

Another solution is that based, for example, on templates of the greyness level of the image as a whole. The most direct comparison (matching) procedure is correlation.

For example, the image can be standardised as described above: each person is represented by a data-bank item which contains a digital image of the front view as well as a set of templates which represent the positions of four windows on the digital image, by their co-ordinates. For example, with reference to FIG. 5: these may be the eyes A, the nose S, the mouth B and the whole face F, that is the region below the eyebrows. During recognition, the data relating to the image detected (obtained from the video signal supplied by the television camera 3) are subsequently compared (in this case, the module 17 also has internal architecture substantially similar to that shown in FIG. 3 with reference to the module 15) with all the images stored in the internal data bank, obtaining as a result a vector of comparison results (one for each characteristic) computed by means of a normalised correlation coefficient. The unknown person is then identified as the person for whom the highest cumulative score is obtained (the scores relating to the different facial characteristics may be integrated using various strategies such as a weighted average, in which the most discriminating characteristics have the greatest weighting, or by selecting the maximum score detected for an individual person. This list is not intended to be exhaustive and variations or similar strategies are intended to be included in this claim.

As an alternative to the correlation coefficient, it is possible to use the distance definition:

$$D_\alpha(x, P_i) = \left( \sum_{a,b} |X(a,b) - P_i(a,b)|^\alpha \right)^{\frac{1}{\alpha}} \quad \text{(IV)}$$

in which the sum is extended to the corresponding pixels of the unknown region X and of the similar region Pi of the i-th person. The remarks made concerning correlation also apply in this case, but it should be noted that the distance has to be minimised (and not maximised as in the case of correlation).

Figure 5:
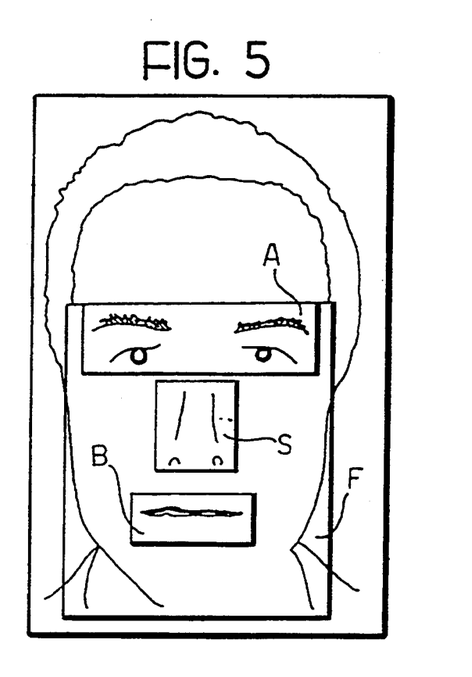

Clearly, one of the elements of greatest interest for the success of this technique is the selection of the windows (e.g. the windows A, B, S and F of FIG. 5).

For example, R. J. Baron's article "Mechanism of Human Facial Recognition", International Journal of Man Machine Studies, 15; 137–138 (1981) proposes that such windows be defined by a human operator in an interactive manner. Naturally, in order to obtain a system suitable for effective practical use it is preferable for this solution to be wholly automatic so that it is possible automatically to form a respective template for insertion in the data bank of the system during training each time the data relating to a new person to be recognised is to be added to the data bank.

The Applicant has also carried out tests relating to the dependence of the recognition process on the resolution of the image available.

In this connection, the performance of the system was checked on a multi-resolution representation of the images available (a Gaussian pyramid of the image preprocessed in a suitable manner). The resolution range was from 1 to 8 (four levels in the Gaussian pyramid, with the maximum resolution corresponding to an interocular spacing of 55 pixels).

It was found that recognition was stable within a range of from 1 to 4 which implies that recognition based on correlation is possible with a good performance level with the use of templates (e.g. the templates A, B, S and F seen above) comprising, for example 36×36 pixels. In this connection, it should be noted that the recognition times are also quite short. For example, the Applicants have found that the time necessary to compare two images with the use of the templates relating to the eyes, the nose and the mouth with an interocular spacing of 27 pixels is about 25 milliseconds operating with a SPARCStationIPX unit.

Another aspect which was analysed by the Applicant is that of establishing the discriminatory powers of individual facial characteristics. Experimental analysis showed that, with reference to the characteristics and the templates considered above, it is possible to establish a graded list of effectiveness which provides, in order, for:

the eyes (template A),
the nose (template S),
the mouth (template B),
the whole face (template F).

In this connection, it can be noted that recognition is quite effective even with reference to only one of the characteristics, which accords with the ability of humans to recognise people known to them even from a single facial characteristic.

Naturally, according to the preferred embodiment, the results obtained with reference to individual facial characteristics can be integrated to obtain an overall score, for example, simply by adding up the scores obtained with reference to the individual characteristics. The integration of several characteristics has a beneficial effect on the effectiveness of the recognition. Performance can be further improved with the use of templates relating to several images of the same person and with the use of combination strategies similar to those proposed for the integration of the data of the various templates, or simply a mean value.

A further iconic strategy which can be applied with advantage is that based on the analysis of the distribution of the greyness levels to permit a comparison of the directional derivatives of the image acquired with those of the images stored (the templates). This method is based on two considerations:

in face-recognition functions, and in object-recognition functions in general, the variations of the shades of grey in the input image convey very useful and discriminatory information, and the derivatives of roundish images are slightly less sensitive to errors of alignment with respect to absolute values.

In this case (again with the use of an architecture of the type shown in FIG. 3) a comparison is made, based on a distance between the directional derivatives of the data of the standardised input image (that is, the face to be recognised) and those stored in a data bank of prototypes or templates which cover all the people known to the system (one or more prototype per person).

The distance measurement used in the method is defined in the following manner. For each image I (x, y) the directional derivative dI (y, x) is computed:

$$dI(y, x) = I(y, x) - I(y-1, x-1)$$

If $I_k(y, x)$ is the image to be recognised, the distance between $I_k((y, x)$ and the J-th template of which the data are stored in the data bank is given by the distance modulo average based on the directional derivatives, on the basis of the following equation:

$$D(k,j) = \sum_{i=1}^{N_j} \frac{|dI_k(y,x) - dP_{ij}(y,x)|}{N_j} \quad (V)$$

in which Pij (y, x) is the I-th image (prototype) of the J-th class in the data bank and Nj is the number of images in the J-th class.

The recognition method then continues by the assignment of $I_k$ (y, x) to the class of the "nearest" prototype in the data bank. This is defined by taking j such that D(k, j) is at a minimum with respect to a fixed threshold $s \geq 0$. If such a j exists, then the face is recognised as that of the j-th person in the data bank. Alternatively, it is rejected as "unknown"; in this case, the system may request the user to repeat the identification operation a second time, for example, by correcting his position in front of the television camera 3. Performance can be further improved with the use of more than one image $I_k(y, x)$ of the person to be recognised.

Moreover, it should be stated that the method described above for withholding recognition can be applied within all the recognition methods referred to in the present description. In other words, the system can be configured so as to withhold recognition when, although the data detected are nearer to one of the templates stored in the data bank than to all the others, their distance from the template is such that recognition is not considered sufficiently reliable.

This method becomes particularly important in verification applications which, as stated several times in the foregoing description, are concerned not with recognising a person from a range of possible people but, on the contrary, with verifying, with a minimal probability of error, that the person P present in front of the system for recognition is actually a certain person and none other. In this application it is thus possible to make the system operate in a manner such that it withholds recognition and verification when the fit of the data detected at the time in question with the template or templates stored in the data bank is inadequate.

As a further variant of the method for iconic recognition strategies, it is possible, again starting from an analysis of the directional derivatives, to convert these derivatives into binary form before making the comparison. Consequently, according to this further way of implementing the subsystem 12, the following steps are envisaged:

standardising the image (as in the case of the strategies examined above),
converting the image into binary form with the use of a suitable binary threshold Tb,
comparing the binary matrix of the image to be recognised with those of the prototypes stored in the data bank of the system,
assigning the image to the class of the nearest prototype in the data bank, provided that the distance is less than an absolute minimum threshold Ta; otherwise it is rejected,
the image is rejected even if the difference between the distance and the second minimum is less than a respective threshold Tr=C/Do in which C is a constant parameter and Do is the actual distance of the first minimum.

Integration of the two recognition functions

As already stated, the system according to the invention is based on the synergistic integration of the results of the recognition functions carried out, on the one hand, by the speech-message recognition sub-system 11 and, on the other hand, by the facial-image recognition sub-system 12.

In general, there are two possible architectures for integrating the results of the two recognition functions. The first integrates the outputs of the two classifiers (recognition subsystems); the second combines the characteristics of the vocal message and of the face directly.

Although the second approach may advantageously be used, the Applicants have found that the first method constitutes an ideal combination of results with ease of execution. This first embodiment can therefore be considered preferred at the moment.

In general, the two subsystems for recognising speech and faces produce independent data.

Various classification methods may be used, according to the specific applications and, in particular to considerations of the cost to be attributed to classification errors (which in turn depend on the application of the system as a whole).

The basic hypothesis is that the conditional probabilities which can be estimated by the speech-recognition subsystem, on the one hand, and by the face-recognition subsystem, on the other hand, are independent of each other. The other important factor is the form selected for the risk expected and this depends on the application and, in particular, on whether it is used for identification or for verification (in the terms recited above).

A general expression for the expected risk Q(f) is as follows:

$$Q(f) = \int_{R^d \times R} V(f(x),y)P(x) \cdot P(y/x)dxdy \quad (VI)$$

(in this connection, see V. N. Vapnik: "Estimation of Dependences Based on Empirical Data", Springer-Verlag, Berlin (1982))
in which the function V is the so-called loss function. If V is quadratic, the expected risk is the normal mean square error and its minimum gives the regression function, that is to say, the conditional average. For a different V, it is possible to obtain the maximum conditional probability P(y|x), the so-called MAP estimate (maximum posterior probability), as an optimal estimate of the expected risk Qo.

It should be noted that, in estimating independent probabilities, $P(y|x) = P(y|x_1)P(y|x_2)$, where $P(y|x_1)$ is the estimated probability for the vocal data and $P(y|x_2)$ is the estimated probability for the face recogniser.

It should be noted that this implies that any network with sufficient approximation capacity (such as, for example, an MLP and an RBF but not a linear perceptron) can learn any estimation (for example, MAP estimation or regression estimation) according to the error function used during training. In the case of identification, the correct V may be the norm $1^2$ with the appropriate unary output representation for the output itself (0 for incorrect correspondence, 1 for correct correspondence).

In the case of verification, the matrix V ("does this image correspond to this template?") requires a three-level output (yes, no, don't know) and should attribute a fairly high score to an incorrect "yes", a lesser score to an incorrect "no", and an even lesser score to a "don't know".

As an example of a simple integration rule of this type, the following algorithm, which may be defined as score integration, is implemented in the system according to the invention.

Both the voice classifier and the face classifier are essentially of the "nearest neighbout" type with suitably defined matrices.

When there is an unknown input, both the classifiers generate (as seen above) a series of possible labels qualified by their distances from the input vector, the distances being computed by equations such as the equations I to VI seen above, as appropriate. The list may be sorted by increasing distances and the first element of the list should thus be considered as the correct correspondence label. The main difficulty in combining the results of the two classifiers is the non-homogeneous nature of the distances produced. Their distance outputs have to be transformed into estimates of the inherent probabilities. The simplest way of solving this problem is by means of a normalisation by the inverse pooled standard deviation. Given the two lists, if $d_{vi}$ and $d_{si}$ represent the distances computed by the face recogniser and by the voice recogniser, respectively (as seen above—equations VI and I) (i indicates the template or prototype with which the comparison is made) and and are the corresponding variances, a combined distance can be defined as:

$$D_i = \frac{dv_i}{\sigma_v} + \frac{ds_i}{\sigma_s} \quad \text{(VII)}$$

in which, of course, $\sigma_v$ and $\sigma_s$ are the respective standard deviations.

A natural way of examining the response of a classifier of the "nearest neighbour" type is to map it as a list of scores against a list of distances.

One possible mapping is as follows:

$$Sv_i = e^{-\frac{dv_i}{\sigma_v}} ; \quad Ss_i = e^{-\frac{ds_i}{\sigma_s}} \quad \text{(VIII)}$$

This mapping associates a distance with a value in the open interval (0, 1). In a certain sense, the higher the score, the more likely it is that the correspondence is correct. Each list can also be normalised by imposing the following condition:

$$\sum_i Sv_i = \sum_i Ss_i = 1 \quad \text{(IX)}$$

The resulting list can be interpreted in a Bayesian manner, suggesting the following integration strategy, upon the hypothesis that the two systems are independent:

$$S_i = S_{vi} \times S_{si} \quad \text{(X)}$$

Since the performances of the two recognition systems are not the same, a weighted merged score may be introduced:

$$S(w)_i = S^w{}_{vi} \times S_{si}{}^{(1-w)} \quad \text{(XI)}$$

where $S(1) = S_{vi}$. The optimal weighting w may be found by maximising the performance of the integrated system on one of the sets of tests available.

Naturally, the principle of the invention remaining the same, the details of construction and forms of embodiment may be varied widely with respect to those described and illustrated, without thereby departing from the scope of the present invention. This applies in particular to the natures of the two (or more) recognition subsystems, the results of which are integrated: in fact the invention may also be applied to subsystems other than the speech and facial-feature recognition sub-systems described above.

What is claimed is:

1. A system for recognizing people comprising:
   means for sensing whether a person is to be recognized;
   a first detector subsystem, responsive to said sensing means, including,
      first detector means for detecting first features including static and dynamic data associated with the person to be recognized,
      a first database including prestored static and dynamic data relating to at least one person to be recognized, and
      means for comparing the detected static and dynamic data with the prestored static and dynamic data and obtaining first distance data;
   a second detector subsystem, responsive to said sensing means, including,
      second detector means for detecting second features associated with the person to be recognized,
      a second database including prestored second features relating to at least one person to be recognized, and
      means for comparing the detected second features and the prestored second features and obtaining second distance data; and
   an integration subsystem including means for combining the first distance data and the second distance data resulting in recognition data, and determining whether the recognition data corresponds to a value related to the prestored static and dynamic data and the prestored second features associated with one person.

2. The system according to claim 1, wherein the combining means sums the first distance data and the second distance data to obtain the recognition data.

3. The system according to claim 1, wherein said integration subsystem recognizes a person whose detected first and second features correspond to the lowest value related to the prestored static and dynamic data and the prestored second features associated with one person.

4. The system according to claim 1, wherein said integration subsystem maps the first and second distance data in accordance with an exponential law and obtains the recognition data as a product of the mapped first and second distance data.

5. The system according to claim 4, wherein according to the exponential law, the first and second distance data are negative exponents so that the mapped first and second distance data are within a finite interval.

6. The system according to claim 4 or 5, wherein the mapped first and second distance data are normalized according to:

$$\sum_i S_{vi} = \sum_i S_{si} = 1$$

7. The system according to claim 4, wherein the recognition data is a weighted merged score according to:

$$S(w)_i = S^w_{vi} * S_{si}^{(l-w)}$$

in which w is selected to maximize performance of said integration subsystem.

8. The system according to claim 1, wherein the first and second distance data have respective variances and are normalized with respect to their standard deviations, the recognition data being calculated from the normalized first and second distance data.

9. The system according to claim 1, wherein the first features correspond to speech features of the person to be recognized and the second features correspond to facial features of the person to be recognized.

10. The system according to claim 1, wherein at least one of said first detector subsystem and said second detector subsystem further includes threshold means for comparing the first or second distance data with at least one threshold value to prevent recognition when the first or second distance data exceeds the at least one threshold.

11. The system according to claim 1, wherein said sensing means detects changes in an environment proximate to the system indicating presence of a person to be recognized.

12. The system according to claim 11, wherein said sensing means receives signals from at least one of said first and second detectors to detect environmental changes.

13. The system according to claim 11, wherein said sensing means receives signals from said second detector to detect environmental changes represented by the detected second features which correspond to facial features of the person to be recognized, said sensing means further including means for activating said first and second subsystems to recognize a person when an image of the detected second features has stabilized for a predetermined period of time.

14. The system according to claim 1, wherein said first subsystem obtains the first distance data in accordance with:

$$d^2(\theta_i, \psi_i) = \sum_{k=1}^{P} \frac{1}{\sigma_k^2} (\theta_{ik} - \psi_{ik})^2$$

in which $\theta_{ik}$ is a first vectorial parameter identifying the first features of the person to be recognized, $\Psi_{ik}$ is a second vectorial parameter identifying a corresponding one of the prestored static and dynamic data in said first database, $\sigma_k^2$ is a mean variance of a k-th component of the parametric vector $(\theta_i, \Psi_i)$ and p is a predetermined constant factor.

15. The system according to claim 14, wherein p is 8.

16. The system according to claim 14, wherein the dynamic data is a first order time derivative of the static data.

17. The system according to claim 16, wherein the static data is based on a time-window analysis of a speech signal.

18. The system according to claim 1, wherein the detected second features of the person to be recognized and the prestored second features include at least one of the following features: eyebrow thickness, distances of eyebrows from an interocular axis corresponding with eyes, arch description of at least one eyebrow, vertical position of a nose, nose width, vertical position of a mouth, lip width, lip thickness, lower jaw description according to radii originating from a mouth center, face width at nose level, and face width at cheekbone level.

19. The system according to claim 18, wherein the second subsystem obtains the second distance data based on a covariance matrix of the second features of the person to be recognized.

20. The system according to claim 1, wherein the detected second features of the person to be recognized and the prestored second features relate to digital representations of portions of a face including at least one of the following portions of the face: the eyes, nose, mouth, and entire face; the digital representations relating to luminous intensity reflected by the at least one portion of the face, the second distance data being obtained by correlating homologous data relating to the detected second features of the person to be recognized and the prestored second features for the at least one portion of the face.

21. The system according to claim 1, wherein the detected second features of the person to be recognized and the prestored second features indicate distribution of greyness levels in a facial image.

22. The system according to claim 21, wherein the second subsystem further comprises means for computing directional derivatives of the facial image.

23. The system according to claim 22, wherein the directional derivatives are converted into binary form prior to being compared.

24. The system according to claim 21, wherein the second subsystem obtains the second distance data in accordance with:

$$D(k_{ij}) = \sum_{i=1}^{N_j} \frac{|dI_k(y,x) - dP_{ij}(y,x)|}{N_j}$$

in which $dI(y,x) = I(y,x) - I(y-1, x-1)$ is the directional derivative of image $I(x,y)$ to be recognized and $P_{ij}(y,x)$ is the i-th image of the j-th of the prestored second features and $N_j$ is the number of images in the j-th class.

* * * * *